US011839608B2

(12) United States Patent
Trela

(10) Patent No.: US 11,839,608 B2
(45) Date of Patent: Dec. 12, 2023

(54) ANTIBACTERIAL PRO-COAGULANT FORMULA

(71) Applicant: Richard Steven Trela, Tampa, FL (US)

(72) Inventor: Richard Steven Trela, Tampa, FL (US)

(\*) Notice: Subject to any disclaimer, the term of this patent is extended or adjusted under 35 U.S.C. 154(b) by 85 days.

(21) Appl. No.: 16/894,723

(22) Filed: Jun. 5, 2020

(65) Prior Publication Data

US 2021/0379045 A1    Dec. 9, 2021

(51) Int. Cl.
| | | |
|---|---|---|
| *A61K 31/455* | (2006.01) | |
| *A61P 31/04* | (2006.01) | |
| *A61K 9/08* | (2006.01) | |
| *A61K 9/00* | (2006.01) | |
| *A61K 8/49* | (2006.01) | |
| *A61K 8/22* | (2006.01) | |
| *A61Q 11/00* | (2006.01) | |
| *A61K 33/40* | (2006.01) | |
| *A61K 9/68* | (2006.01) | |
| *A61K 9/70* | (2006.01) | |
| *A61K 9/06* | (2006.01) | |
| *A61Q 7/00* | (2006.01) | |

(52) U.S. Cl.
CPC .............. *A61K 31/455* (2013.01); *A61K 8/22* (2013.01); *A61K 8/4926* (2013.01); *A61K 9/0014* (2013.01); *A61K 9/0058* (2013.01); *A61K 9/06* (2013.01); *A61K 9/08* (2013.01); *A61K 9/7015* (2013.01); *A61K 33/40* (2013.01); *A61P 31/04* (2018.01); *A61Q 7/00* (2013.01); *A61Q 11/00* (2013.01); *A61K 2800/70* (2013.01); *A61K 2800/87* (2013.01); *A61K 2800/92* (2013.01)

(58) Field of Classification Search
CPC ......... A01N 59/16; A61Q 11/00; A61K 33/40
USPC .................................................... 424/49, 53
IPC ..................................................... A61Q 11/00
See application file for complete search history.

(56) References Cited

U.S. PATENT DOCUMENTS

| | | | | |
|---|---|---|---|---|
| 4,537,778 A | * | 8/1985 | Clipper | A61K 8/37 424/53 |
| 6,660,289 B1 | * | 12/2003 | Wilmotte | A61P 1/02 424/605 |
| 2015/0118644 A1 | * | 4/2015 | Cohen Tanugi | A61C 19/06 433/88 |
| 2019/0175956 A1 | * | 6/2019 | Dolezal | A61K 8/99 |

FOREIGN PATENT DOCUMENTS

KR    1020160181078    *    5/2018    ......... A61K 31/4406

OTHER PUBLICATIONS

Heinz, "Heinz All Natural Apple Cider Vinegar 5% Acidity 32 fl oz Bottle." www.heinz.com. Published online Aug. 30, 2018 (Year: 2018).*

\* cited by examiner

*Primary Examiner* — Walter E Webb
(74) *Attorney, Agent, or Firm* — Stefan V. Stein

(57) ABSTRACT

The disclosed invention provides an antibacterial pro-coagulant formula for assisting in combating the condition of bleeding gums caused by periodontal disease and gingivitis that enhances the natural healing process by assisting in the of cessation of bleeding by providing an "anti-bacterial oral healing environment" accompanied by enhanced blood flow to the affected bleeding area for more rapid blood clotting and increased blood flow to the affected area to assist the body's natural process of rebuilding healthy gum-tissue. Additionally, the disclosed invention with its antibacterial benefits, when used topically, provides for rapid surface skin blood clotting as well as increased blood circulation on the skin surface which greatly aids in the healing of external skin cuts, such as nicks from shaving or against inflammation of the skin from acne vulgaris. Continued use of the product orally and topically has proven to provide a beneficial stability to overall oral and skin health, especially useful in promoting healing in high-bacterial environments, such as is common in a person's mouth or on their face. Further described is a method of promoting hair follicle growth by application of the presented invention to a human scalp to promote blood flow to the scalp through below skin surface blood vessel dilation and below surface anti-bacterial cleansing of the scalp effecting an unrestricted and healthy skin tissue environment conducive to promoting hair follicle re-growth.

12 Claims, 4 Drawing Sheets

Figure 3:
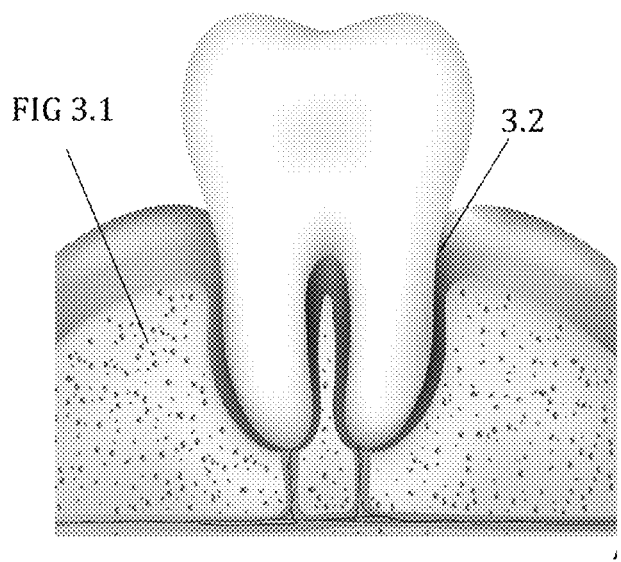

FIG 3- Shows the now recovered gum structure with the gums grown back to healthy state. FIG 3.1 shows the now healthy gums and 3.2 shows the gums now tight against the tooth.

Figure 4:
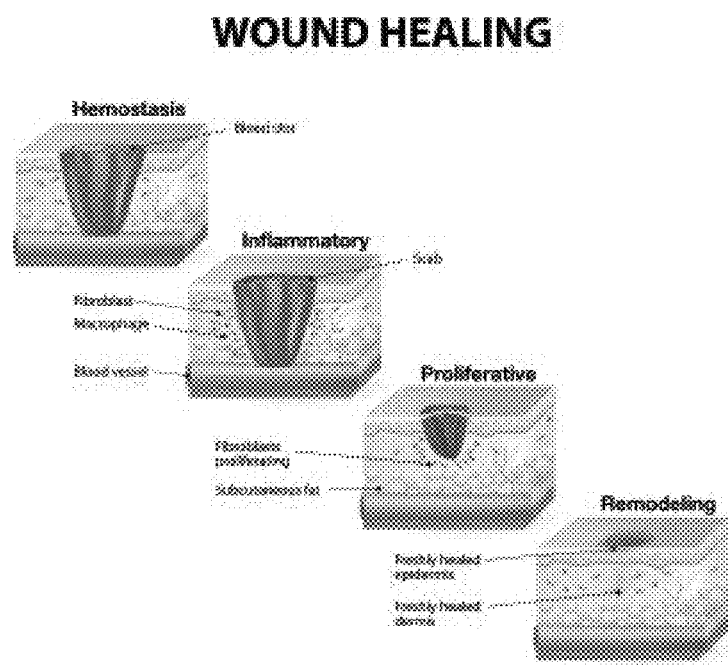

FIGURE 4 is an illustration that shows the 4 stages of wound healing. 4.1 is the Hemostasis stage. 4.2 is the Inflammatory stage. 4.3 is the Proliferative stage and 4.4 is the Remodeling stage.

ANTIBACTERIAL PRO-COAGULANT FORMULA

STATEMENT OF FEDERALLY SPONSORED RESEARCH

N/A

FIELD OF INVENTION

The presented invention relates to oral care and more specifically to an antibacterial pro-coagulant composition for gum care and for use in the treatment of gingivitis, bleeding gums, gum inflammation and periodontal disease. Additionally, the invented formula provides a breakthrough in the field of topical treatments for acne, skin rejuvenation, insect bite relief and first aid for stopping bleeding from razor nicks. Further described is a method of promoting hair follicle growth by application of the presented invention to a human scalp to promote blood flow to the scalp through below skin surface blood vessel dilation and below surface anti-bacterial cleansing of the scalp effecting an unrestricted and healthy skin tissue environment conducive to promoting hair follicle re-growth.

BACKGROUND OF THE INVENTION

Dental plaque is a sticky biofilm or a mass of bacteria that is commonly found between the teeth, along the gumline, and below the gumline margins. Dental plaque can give rise to dental caries and periodontal problems, such as gingivitis and periodontitis. In the early stages, periodontitis has very few symptoms, and in many individuals the disease has progressed significantly before they seek treatment. Symptoms may include redness or bleeding of gums while brushing teeth, using dental floss or biting into hard food. Other symptoms include gum-swelling that recurs, spitting out blood after brushing teeth, halitosis, or bad breath, and a persistent metallic taste in the mouth. Deep-pockets between the teeth and the gums, and loose teeth occur in the later stages.

Deep teeth-cleaning, also referred to as root planing or scaling, is a procedure carried out by a dental hygienist to treat periodontal and gum disease. The scaling process scrapes away bacterial plaque and tartar from the tooth. Sometimes, deep teeth-cleaning results in or furthers inflammation of the gums. In a regular cleaning, scaling is performed on the part of the tooth that is exposed above the gumline.

A deep-cleaning is a periodontal procedure used to treat early-stage periodontal (gum) disease. A dentist, periodontist (gum specialist), or dental hygienist removes the plaque through a deep-cleaning method that combines scaling and root planing. Scaling is performed above and below the gumline to remove plaque and tartar. Root planing gets rid of rough spots on the tooth where germs gather, and helps remove bacteria that contribute to gum disease.

Although deep-cleaning is effective at removing plaque buildup, it does not eliminate all the bacteria that cause gum disease. Currently, when necessary, treatment may also include placing medication such as Arestin or Perio-Chip into gum pockets if the pocket is greater than 4 mm. In that case, patients are advised to postpone brushing for 12 hours and avoid the use of inter-proximal cleaning devices (flossing) for 10 days.

It is this recovery period of time after periodontal treatment in which, due to the inflammation and open wounds caused by the deep-cleaning procedure itself, that a "bacteria free" healing environment is needed for natural gum healing. All too often, the patient fails to achieve lasting results due to the fact that there has not been, until now, a workable system to provide a "bacteria-free enough" and healthy enough oral environment, long enough, to allow the gums a chance to heal naturally.

It would be similar to having an open wound on the body. If it were open and bleeding, and it was not allowed to go through the natural healing stages of the cessation of bleeding, followed by the healing of the inflammation and then onto its healthy tissue re-growth stage, (due to the open wound being in a wet environment under constant bacterial attack, like the environment gums are exposed to after periodontal treatment), of course the healing process itself, would, at best, be a source of further health and healing complications due to infection, protracted exposure to the bacterial environment, as well as being painful to the patient.

The presented invention with its active indigents combined and administered as described herein, has exceptional anti-bacterial, anti-inflammatory, and deep-cleansing benefits on patients who recently had their teeth professionally deep-cleaned by a dentist or hygienist. The presented invention provides a breakthrough anti-bacterial and pro-coagulant "oral healing environment" that is greatly efficacious in the restoration of gums from a periodontal "emergency state" of bleeding gums, to a reinstated natural healthy condition that provides the desired "fresh start", so many of today's periodontists, dentists and hygienists are desiring for their trusting oral care patients.

4 Main Gum Healing Phases:

Gum healing can be divided into 4 overlapping phases: Hemostasis, Inflammatory, Proliferative and Maturity Phase 1: Hemostasis Phase Hemostasis, the first phase of healing, could be said to begin at the onset of injury, and the objective is to stop the bleeding. In this phase, the body activates its emergency repair system, namely the blood clotting system, and forms a dam to block the drainage. During this process, platelets come into contact with collagen, resulting in activation and aggregation. An enzyme called thrombin is at the center, and it initiates the formation of a fibrin mesh, which strengthens the platelet clumps into a stable clot.

Phase 2: Defensive/Inflammatory Phase

Phase 1 is primarily about coagulation, the second phase, could be called the Defensive/Inflammatory Phase and it focuses on destroying bacteria and removing debris-essentially preparing the wound bed for the growth of new tissue.

During Phase 2, a type of white blood cells called neutrophils enter the wound to destroy bacteria and remove debris. These cells often reach their peak population between 24 and 48 hours after injury, reducing greatly in number after three days. As the white blood cells leave, specialized cells called macrophages arrive to continue clearing debris. These cells also secrete growth factors and proteins that attract immune system cells to the wound to facilitate tissue repair. This phase often lasts four to six days and is often associated with edema, erythema (reddening of the skin), heat and pain.

Phase 3: Proliferative Phase

Once the wound is cleaned out, the wound could b e said to enter Phase 3, the Proliferative Phase, where the focus is to fill and cover the wound.

The Proliferative phase features three distinct stages: 1) filling the wound; 2) contraction of the wound margins; and 3) covering the wound (epithelialization).

During the first stage, shiny, deep red granulation tissue fills the wound bed with connective tissue, and new blood vessels are formed. During contraction, the wound margins contract and pull toward the center of the wound. In the third stage, epithelial cells arise from the wound bed or margins and begin to migrate across the wound bed in leapfrog fashion until the wound is covered with epithelium.

Phase 4: Maturation Phase

During the Maturation phase, the new tissue slowly gains strength and flexibility. Here, collagen fibers reorganize, the tissue remodels and matures and there is an overall increase in tensile strength (though maximum strength is limited to 80% of the pre-injured strength). The Maturation phase varies greatly from wound to wound, often lasting anywhere from 21 days to two years.

The healing process is remarkable and complex, but it is also susceptible to interruption due to local and systemic factors, including moisture, bacterial infection, and maceration.

The presented invention when used as described herein provides a greatly improved antibacterial and pro-coagulant healing environment due to increased blood circulation and improved clotting to more a rapidly assist the body through the 4 main healing phases to heal and replace devitalized gum and skin tissue.

BRIEF SUMMARY

Disclosed herein is an anti-bacterial and pro-coagulant composition that includes (a) (NIACIN) Pyridine-3-Carboxylic Acid, (b) (HYDROGEN PEROXIDE) and optionally (c) Dihydrogen Dioxide, (DISTILLED WATER) Dihydrogen Oxide, potable water or purified water, (d) (CALCIUM) Calcium 7440-70-2 and optionally (e) (VITAMIN D3) Cholecalciferol. In some embodiments, the oral and topical care antibacterial pro-coagulant composition can be in the form of a liquid, paste, gel, spray, gum or other excipient.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

SUMMARY

Hydrogen Peroxide kills bacteria by oxidizing their cell walls, stealing electrons from them and disrupting their chemical structures. Niacin is required for the proper function of fats and sugars in the body and to maintain healthy cells. Niacin also causes the small blood vessels on the skin and in the gums to dilate so more blood can rush to an area affected by skin inflammation, gingivitis or periodontal inflammation or injury due to dental deep-cleaning tools and procedures. At higher doses, niacin has beneficial effects on speed of blood clotting. It has now been discovered that niacin, when dissolved and placed in formulation with hydrogen peroxide, and when used as described herein, is effective in fighting gum-disease, aids in stopping gum-bleeding and gum-inflammation, and can simultaneously provide an effective concentration of Niacin to promote enhanced blood circulation and clotting to the injured or inflamed gum tissue, as well as provide an enhanced anti-bacterial and increased blood flow environment for gum tissue rehabilitation. Optionally used along with the basic inventive combination of Niacin and Hydrogen Peroxide, as an additional benefit, distilled water can be added which is effective in removing toxins in the body and is soluble and combines well with Niacin and Hydrogen Peroxide. Additionally, Calcium which is beneficial in bone growth and strength, and vitamin D3 which assists in the body's absorption of Calcium can also be added as described herein to provide vital building blocks for bone-strengthening and natural tissue and bone re-growth.

EXAMPLES OF DENTAL PATIENT USE OF THE PRESENTED INVENTION DURING PERIODONTAL DISEASE RECOVERY STAGES

Phase 1: Hemostasis Phase

When brushing or flossing, if bleeding gums occur, use the current invention as follows: add ⅔ parts of current invention and ⅓ part distilled water to your water jet flossing machine tank. Set pulse as high as comfortable and concentrate pulse irrigation on problem gum areas first. Lean over sink and spend the 1st % of the tank drain time on known deep pocket gum areas, working to get a deep rinse on each pocket. Next, power rinse along the entire gum-line of both upper and lower gums, both inside and out. When the tank is empty, continue to lean over the sink and allow the presented invention formula to foam out bacteria and particles freely from your mouth. This may foam for some time, so be patient until foaming ceases. When foaming has subsided, brush teeth and rinse thoroughly after brushing. Repeat daily, in the morning and again at night, until the bleeding phase is cleared.

2: Defensive/Inflammatory Phase

Once the bleeding phase has passed, the presented invention greatly assists in destroying harmful bacteria and removing deep food debris helping clear the way for inflamed gums to grow healthy and strong. In Phase 2, add a ½ ratio part of the presented invention formula and ½ part distilled to your water jet flossing machine tank. Repeat procedure as in Phase 1.

Phase 3: Proliferative Phase

The presented invention assists in the re-growth of healthy gums by providing a healthy oral environment which continues to defend against harmful bacteria growth and assists the body it's natural recovery process. In Phase 3, use ⅓ the presented invention and $\frac{2}{3}^{rds}$ distilled water in the water jet flossing machine tank and follow the same procedure as Phase 1, and 2 for use.

Phase 4: Maturation Phase

During the Maturation phase, the new tissue slowly gains strength and flexibility. The presented invention assists in the re-growth of healthy gums by providing a healthy oral environment by continuing to defend against harmful bacteria growth and assists the body's natural recovery process. In Phase 4, use a ratio of ¼ of the presented invention to ¾ distilled water in the water jet flossing machine tank and follow the same procedure as Phase 1, 2, and 3 for use.

DRAWING FIGURES

Figure 1:
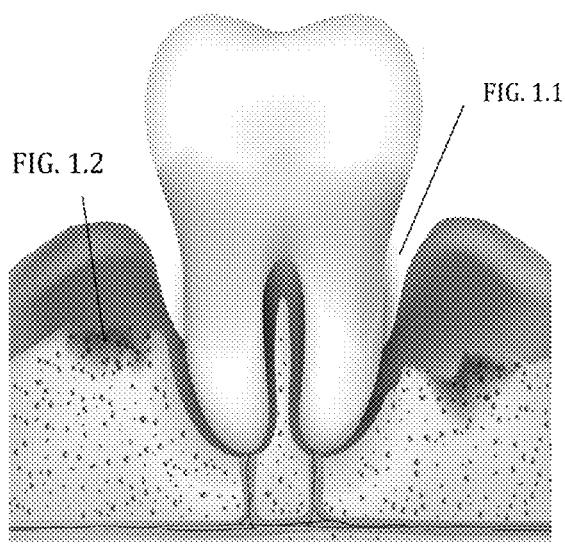
FIG 1 shows a human tooth with gums that have receded away from the tooth due to bacterial decay. 1.1 shows a gap between the tooth and 1.2 shows bacteria in the gums.

FIG. 1—shows a human tooth with gums that have receded away from the tooth due to bacterial decay. 1.1 shows a gap between the tooth and 1.2 shows bacteria in the gums.

Figure 2:
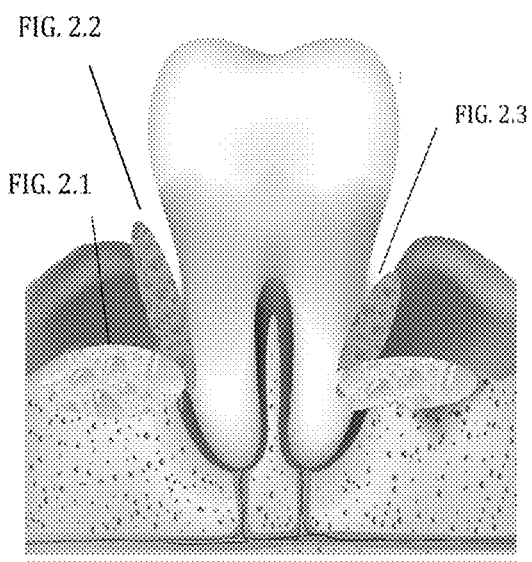
FIG 2 shows the presented invention filling the gaps with the Niacin and Peroxide formula. 2.1 shows the formula attacking the bacteria, 2.2 and 2.3 shows the formula filling the gap and soaking the bacteria laden gun area.

FIG. 2 shows the presented invention filling the gaps with the Niacin and Peroxide formula. 2.1 shows the formula attacking the bacteria, 2.2 and 2.3 shows the formula filling the gap and soaking the bacteria laden gun area.

FIG. 3—Shows the now recovered gum structure with the gums grown back to healthy state. FIG. 3.1 shows the now healthy gums and 3.2 shows the gums now tight against the tooth.

FIG. 4 is an illustration that shows the 4 stages of wound healing. 4.1 is the Hemostasis stage. 4.2 is the Inflammatory stage. 4.3 is the Proliferative stage and 4.4 is the Remodeling stage.

The invention claimed is:

1. A method for treatment of bleeding gums caused by periodontal disease or gingivitis comprising jetting the bleeding gums with an antibacterial pro-coagulant, said antibacterial coagulant comprising (a) 0.01 wt % to 3 wt % Pyridine-3-Carboxylic Acid and (b) 97.00 wt % to 99 wt % Hydrogen Peroxide, wherein said percentages are based on the total weight of the antibacterial pro-coagulant; and repeating said letting at least once per day until gum tissue remodels and matures, resulting in an overall increase in tensile strength.

2. The method of claim 1, further comprising water.

3. The method of claim 1, wherein the Dihydrogen Oxide (Distilled Water) or optionally water is present in the antibacterial pro-coagulant composition in a concentration of 0.1 wt % to 75 wt % based on the total weight of the antibacterial pro-coagulant.

4. The method of claim 1, further comprising either calcium carbonate or calcium citrate.

5. The method of claim 1, wherein the calcium carbonate or calcium citrate is present in the antibacterial pro-coagulant composition of 0.001 wt % to 3 wt %, based on the total weight of the antibacterial pro-coagulant.

6. The method of claim 1, further comprising Vitamin D-3.

7. The method of claim 6, wherein the Vitamin D-3 is present in the antibacterial pro-coagulant composition in a concentration of 0.001 wt % to 3 wt %, based on the total weight of the antibacterial pro-coagulant.

8. The method of claim 1, further comprising a food grade acidic agent, with an acidity level of 4-6%.

9. The method of claim 8, wherein the food grade acidic agent with an acidity level of 4-6% is present in the antibacterial pro-coagulant composition in a concentration of 0.01 wt % to 15 wt %, based on the total weight of the antibacterial pro-coagulant.

10. The method of claim 1, wherein the anti-bacterial pro-coagulant suspended in an excipient medium in the form of a liquid, or spray.

11. The method of claim 1, further comprising orally-acceptable excipients.

12. The method as set forth in claim 1, wherein the step of jetting comprises filling a water jet tank with said antibacterial pro-coagulant and jetting said antibacterial pro-coagulant into the bleeding gums.

* * * * *